United States Patent

Wood et al.

[11] Patent Number: 5,097,698
[45] Date of Patent: Mar. 24, 1992

[54] DETECTION METHOD FOR DETERMINING PHASE BOUNDARIES

[75] Inventors: Robert H. Wood, Newark, Del.; Rosa Crovetto, Gaithersburg, Md.; Vladimir Mayer, Chamalieres, France

[73] Assignee: University of Delaware, Newark, Del.

[21] Appl. No.: 540,053

[22] Filed: Jun. 19, 1990

[51] Int. Cl.⁵ .............................................. B01N 11/02
[52] U.S. Cl. ........................................................ 73/54
[58] Field of Search ............... 73/19.03, 61.1 R, 61 R, 73/64.2, 54, 64.1; 210/746, 739, 96.1

[56] References Cited

U.S. PATENT DOCUMENTS

| | | | |
|---|---|---|---|
| 3,253,711 | 12/1962 | Young | 210/96.1 |
| 3,903,731 | 9/1975 | Sieben | 73/54 |
| 3,913,383 | 10/1975 | Kreula et al. | 73/54 |
| 4,148,216 | 4/1979 | Do et al. | 73/64.1 |
| 4,838,084 | 6/1989 | Leepold et al. | 73/32 A |
| 4,972,724 | 11/1990 | Ricken | 73/861.37 |

Primary Examiner—Hezron E. Williams
Assistant Examiner—Shu-Cheng Kau

[57] ABSTRACT

A novel method for detecting phase transitions depends on an observed sharp drop in the amplitude of vibration of a vibrating tube containing test material when phase transitions occur. Combining phase equilibria detection with conventional density measurement permits the exploration of pressure, volume, temperature and composition at phase boundaries. The method is especially useful at high temperatures and pressures.

1 Claim, 1 Drawing Sheet

DETECTION METHOD FOR DETERMINING PHASE BOUNDARIES

The government of the United States of America has certain rights in this invention by virtue of National Science Foundation Grant Number 90 21 CHE 87 12204.

BACKGROUND OF THE INVENTION AND PRIOR ART

An accurate knowledge of the phase equilibria boundary of pure components and/or mixtures is not only a matter of fundamental scientific interest. It is very important for test of proposed equations of state, (EOS), pair potentials, mixing rules, etc. It is also of great practical importance for geochemistry, for power generation and for many chemical engineering processes.

There are two recent reviews on techniques and methods on high pressure PVT data and phase equilibria measurements by Schneider and Deiters Fluid Phase Equilibria 29 145-160 (1986) and by Marsh et al. Fluid Phase Equilibria 29 161 (1986).

The well-known PT vapor-liquid coexistence line of pure water was used to test the behavior of the phase detector and to establish the best experimental procedure to follow. The performance of thsi new detection method was then assessed with measurements of bubble points for pure water and for sodium chloride solutions. Many other kinds of phase separations can also be detected and measured in accordance with this invention.

SUMMARY OF THE INVENTION

The method of detecting the separation of a fluid into two or more phases comprising the use of the change in the ratio of vibrating amplitude to the drive power of a vibrating tube to detect the phase separation. The vibrating tube contains the fluid to be measured.

DESCRIPTION OF THE PREFERRED EMBODIMENT

During measurements of the densities of aqueous alkali metal salt solutions with a vibrating tube densimeter, we noticed that the amplitude of the vibration (at constant drive power) changed either when there was a large change in viscosity of the fluid or when the tube contained two phases. The densimeter used was similar to the one described by Wood and Albert, *Review of Scientific Instruments* 55, 589 (1984).

For our apparatus the appearance of a liquid-gas transition in the fluid produces a maximum decrease of about 5 to 10% in the amplitude of the pick-up signal at constant drive power. For ease of observation the amplitude differences between a constant base line and the rectified and amplified pick-up signal was displayed on a strip chart recorder.

Figure 1:
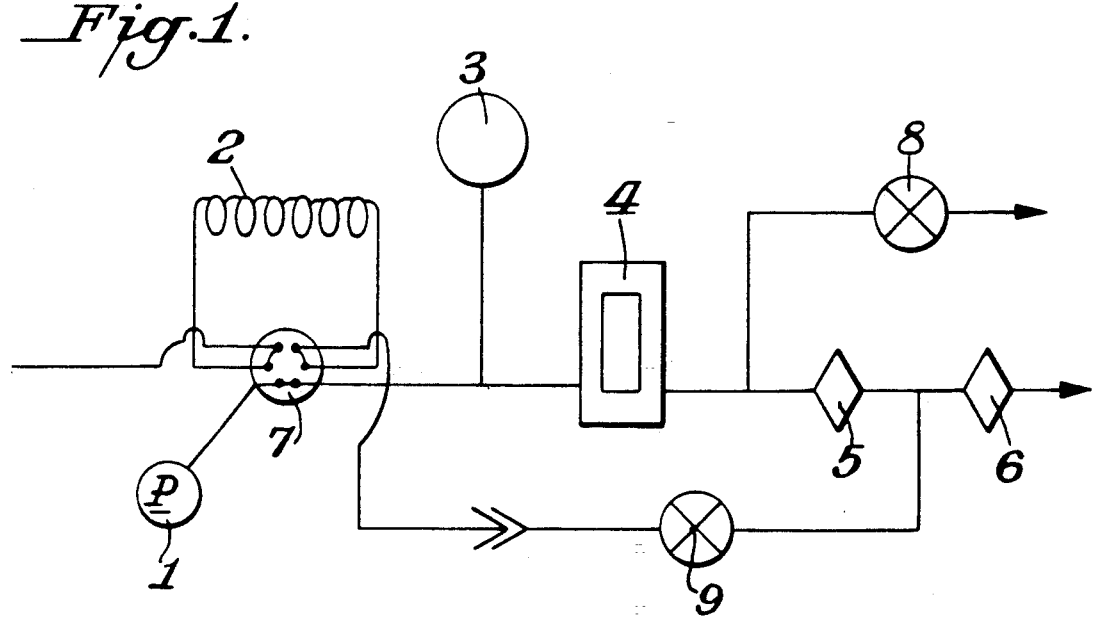

FIG. 1 depicts schematically the set up used in the measurements; 1, Constametric HPLC pump; 2, 6 cm$^3$ injection loop; 3, Paroscientific Digiquartz manometer; 4, vibrating tube and its housing; 5 and 6, Circle Seal BPR 21 series back pressure regulators; 7, Rheodyne 7010 HPLC six port injection valve; 8, needle valve for decreasing pressure in the system; 9, prepressurising valve.

A phase transition in the fluid is produced by changing any of the variables P, T or x or any combination of them. For our apparatus and set-up an efficient way to work is to maintain constant fluid composition and temperature and to produce the new phase by a pressure change.

Figure 2:
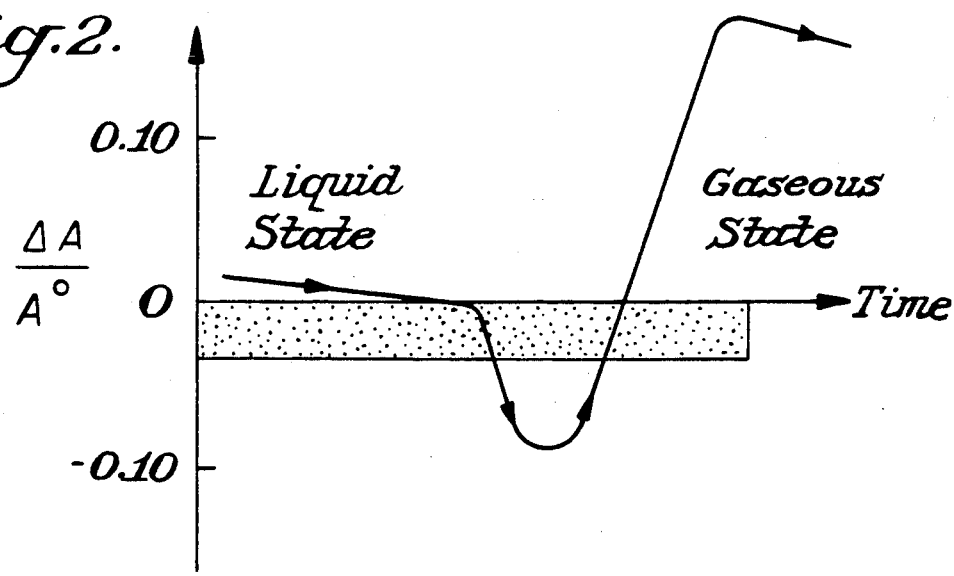

FIG. 2 Schematic representation of a typical time evolution of the pick-up amplitue, A, of the vibrating tube plotted as $(A-A°)/A° = \Delta A/A°$ where A° is an arbitrary constant. In this experiment the needle valve 8 was opened and $\Delta A/A°$ was followed as a function of time. The noise level, 0.1-0.2%, is not shown. The shaded area shows typical amplitude changes after arresting the pressure drop.

Figure 3:
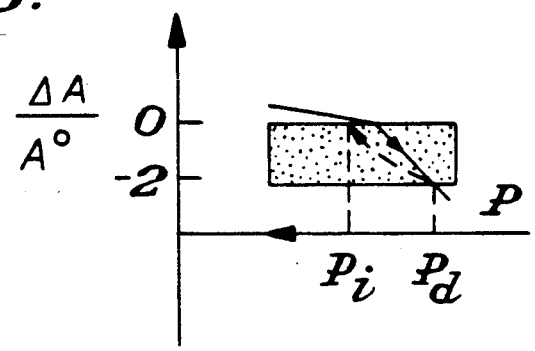

FIG. 3. $\Delta A/A°$ vs P, the steady state pressure, for small changes in the amount of fluid in the tube. Note that P increases toward the left. Dotted curve for infusion of fluid, full curve for withdrawal. For definitions of $P_i$ and $P_d$, see below.

In the case of a phase separation the energy dissipation in the two phase fluid appears to be the cause of the drop in amplitude. Thus the magnitude of the decrease in the amplitude is related to the relative quantity of the two phases present. It is important to keep the newly generated phase as small as possible, especially with mixtures, in order not to alter the concentration of the initial phase. This is done by halting the pressure drop as soon as a detectable amplitude decrease has been observed (shaded area in FIGS. 2 and 3). The vibration of the tubing helps equilibration.

Inherent to any phase separation there are important kinetic and thermal effects. They must be experimentally considered and carefully examined, especially when working under static conditions and without proper stirring. Supersaturation and overheating when condensing and supercooling and undersaturation when evaporating are commonly observed with different techniques. In order to assess the magnitude of these problems in the present apparatus, the reproducibility of the pressure at which phase appearance and disappearance occurred was studied using pure water as a test fluid.

A typical run for water starts with water flowing in the apparatus at 0.1-0.2 cm$^3$·min$^{-3}$ and at a pressure 5-10 bars above its vapor pressure. The flow was stopped and by opening carefully and slowly valve 8, the rate of pressure decrease was adjusted to a desired value, and the amplitude was recorded. The noise level in the amplitude was about 0.1%. When the amplitude dropped by 1 to 3% (shaded area FIGS. 2 and 3), valve 8 was closed and the corresponding pressure value was noted. The pressure slowly increased to a steady state value in the next 10 to 20 minutes. This pressure is reported as the "steady state" phase boundary pressure for decreasing pressure ($P_d$) (see FIG. 3). Next the pressure was increased with a very small flow from the pump, less than 0.1 cm$^3$·min$^{-1}$. The pump was stopped when the pick-up signal increased more than 5 times the noise level. After 10 to 20 minutes the pressure and amplitude came to steady state values. The pressure increases were repeated until the steady state amplitude was equal to or higher (within the noise level) than the amplitude just before the appearance of the second phase with decreasing pressure. This pressure was taken as the "steady state" pressure for phase disappearance with increasing pressure ($P_i$) (see FIG. 3). With the pump switched on again, fresh water was introduced in the vibrating tube. After the pressure increased to the initial value (5-10 bars above the water pressure at that temperature) the flow was stopped and the whole procedure repeated.

It was found that $P_d$ was always smaller than the known equilibrium pressure of pure water, $P^o$, at the temperature of the block. The velocity at which the pressure was changed played a very important role in $P_d$. With rapid pressure changes, the difference between $P_d$ and $P^o$ increased, apparently due to lack of equilibration. Below certain velocity values (0.2 to 0.3 bar·min$^{-1}$ in our experiments) the experiment took longer and did not yield higher accuracy. There appears to be an optimum velocity for each fluid. In our experiments values obtained for $P_d$ at near optimum rates were $-0.25\%$ to $-0.88\%$ smaller than $P^o$. $P_i$ was always greater than $P_d$, almost always greater than $P^o$, and less dependent on the velocity of the pressure increase. The observed difference, $P_i-P^o$, varied from from $-0.2\%$ to 2%. The greater spread in differences between $P_i$ and $P^o$ reflects the greater experimental difficulty in measuring $P_i$.

For pure water the pressure average $P_{av}=(P_d+P_i)/2$ gave the best agreement with the known values for vapor pressure of water, $P^o$(Haar et al. *NBS/NRS Steam Tables: Thermodynamic and Transport Properties and Computer Programs for Vapor and Liquid States of Water in SI Units*, Hemisphere Publishing Corp. Washington, D.C. (1984) 1983) at the experimental temperature.

For water we measured, bubble points as described above, and also a dew point (Table 1) For the dew point we started at an initial pressure about 5 bars below the vapor pressure of water at that temperature and we measured in the same way first the steady state pressure for phase appearance, $P_i$, by slowly increasing the pressure, and then the steady state pressure for phase disappearance, $P_d$, by slowly decreasing the pressure. Within experimental error the measured dew point was equal to the bubble point but the difference $P_i-P_d$ was somewhat higher than for the bubble point measurements.

TABLE 1

| T/°C. | Measured Vapor Pressure of Pure Water | | | |
|---|---|---|---|---|
| | $P_{av}$/MPa[a] | Δ/MPa[b] | P*/MPa[c] | δ[d] |
| 325.17 | 12.05 | 0.01 | 12.07 | −0.17 |
| 333.57 | 13.44 | 0.09 | 13.45 | −0.07 |
| 333.80 | 13.44 | 0.03 | 13.49 | −0.37 |
| 341.23 | 14.79 | 0.04 | 14.82 | −0.20 |
| 344.56 | 15.44 | 0.06 | 15.45 | −0.06 |
| 344.71[e] | 15.49 | 0.46 | 15.48 | 0.07 |
| 347.04 | 15.90 | 0.01 | 15.93 | −0.19 |
| 349.72 | 16.60 | 0.27 | 16.47 | 0.79 |
| 349.73 | 16.47 | 0.12 | 16.47 | 0.00 |
| 349.73 | 16.59 | 0.29 | 16.47 | 0.35 |
| 349.75 | 16.58 | 0.24 | 16.47 | 0.67 |
| 349.75 | 16.52 | 0.18 | 16.47 | 0.30 |
| 349.78 | 16.54 | 0.16 | 16.48 | 0.36 |
| 349.91 | 16.56 | 0.17 | 16.50 | 0.36 |
| 349.93 | 16.45 | 0.05 | 16.51 | −0.36 |
| 350.28 | 16.64 | 0.19 | 16.58 | 0.37 |
| 350.28 | 16.65 | 0.28 | 16.58 | 0.43 |
| 350.28 | 16.59 | 0.21 | 16.58 | 0.06 |
| 350.28 | 16.53 | 0.21 | 16.58 | −0.30 |
| 350.28 | 16.52 | 0.20 | 16.58 | −0.36 |
| 350.28 | 16.47 | 0.04 | 16.58 | −0.66 |
| 362.91 | 19.28 | 0.01 | 19.32 | −0.21 |

[a] $P_{av}=(P_i+P_d)/2$
[b] $\Delta=(P_i-P_d)/2$
[c] P* = pure water vapor pressure from Steam Tables (Haar et al., 1984)
[d] $\delta=100(P_{av}-P^*)/P^*$
[e] dew point. All other measurements are bubble points.

To measure a solution vapor pressure; a NaCl solution of known concentration was introduced into the system using the injection valve 7 with a flow of 0.2–0.3 cm$^3$·min$^{-1}$. The procedure from there on was the same as with water. Each 6 cm$^3$ of injection allowed 3 to 4 different measurements with fresh solution inside the vibrating tube.

The variation of the fluid density with pressure exhibited discontinuity in the slope at the appearance of the second phase. The period of vibration is related to the density by $$\Delta\rho = K(\tau^2 - \tau_0^2)$$

where rho is density, K is the calibration constant, and tau is the period of vibration. Measuring the period as a function of pressure was not as accurate, reproducible or rapid as measuring the amplitude change for detecting a change in the number of phases with the present apparatus. Sudden irreversible shifts in frequency sometimes occur when the pressure is varied, so discontinuities in period vs pressure might be observed that are spurious effects. Also period measurements are much slower because averaging the period of vibration over about one minute is necessary so that the pressure variations must be much slower in order to get representative period readings.

The temperature was measured in the block that housed the vibrating tube with a calibrated Burns therometer, accuracy of about 0.1 K. The constancy of the temperature was ±0.01 K. At 623 K. the variation of the vapor pressure of pure water with temperature is about 0.19 bar/0.1 K., so that our temperature imprecision of 0.1 K. will translate to about a 0.2% error in the vapor pressure of water. The pressure was measured with a Paroscientific digiquartz manometer with a manufacturer's calibration accuracy 0.01%. The water used was deionized and degassed. The NaCl was Fischer Scientific ACS. Solutions were made by weighing the dry salt and the water. The accuracy in concentration was 0.1% for the 1 mol·kg$^{-1}$ NaCl and 0.03% for the 3 mol·kg$^{-1}$ NaCl solutions, respectively.

Table 1 gives the measurement of vapor pressure for water at different temperatures presented as $P_{av}$ and Δ, where $\Delta=(P_i-P_d)/2$. The vapor pressure of water $P^o$ and the deviation of the present measurements from $P^o$ is also given. Our average deviation of a single measurement from the literature value, calculated as $$\sum_i (P_{av} - P^*)/(N-1)P^*$$

is 0.32% and the reproducibility of individual measurements is normally around ±0.4% (occasionally ±0.7%).

In Table 2 we present the results obtained for the salt solutions at an almost constant temperature, near 623 K. Table 2 gives $P_{av}$, Δ, the literature value, and the corresponding deviation from the literature value. The reproducibility of measurements is about ±0.5%. Literature values have been taken from a smooth curve through the results of Bischoff et al. (1989) Amer. J. of Science 289: 217-248, Olander et. al. (1950) Acta Chemica Scandanavia, 4: 1437–1445, Khaibullin et al. (1966) Teplofix. Vysokikh Temperature 4: 518–521, and Valyashko et al. (1986) Obzori Poleplophizicheskim Svoisvan Veska 4(60): 1–114 with more weight given to the more recent compilation of Bischoff et al.

TABLE 2

| T/°C | Vapor Pressure for NaCl(aq) | | | |
|---|---|---|---|---|
| | $P_{av}$/MPa[a] | $\Delta$/MPa[b] | $P^r$/MPa[c] | $\delta^d$ |
| | m = 3.0 mol·kg$^{-1}$ | | | |
| 349.97 | 14.89 | 0.15 | 14.83 | 0.40 |
| 349.97 | 14.79 | 0.02 | 14.83 | −0.27 |
| 349.97 | 14.74 | 0.23 | 14.83 | −0.61 |
| 349.97 | 14.80 | 0.28 | 14.83 | −0.20 |
| 349.97 | 14.77 | 0.17 | 14.83 | −0.41 |
| | m = 1.0 mol·kg$^{-1}$ | | | |
| 349.94 | 15.87 | 0.22 | 15.91 | −0.25 |
| 349.97 | 15.81 | 0.10 | 15.91 | −0.60 |

[a] $P_{av} = (P_i + P_d)/2$
[b] $\Delta = (P_i - P_d)/2$
[c] Literature values for the vapor pressure of the solution at 350°C (see text). For 3 mol·kg$^{-1}$ NaCl there is about a 1% scatter in the vapor pressure measured in different laboratories, for 1 mol·kg$^{-1}$ the scatter is about 0.3%
[d] $\delta = 100 (P_{av} - P^r)/P^r$ The tables show that the results given by the presented detection method are in good agreement with previous results.

This new detection method for phase boundaries is quick and reasonably accurate for measuring the vapor pressure of solutions at high temperatures. It can be easily automatized and used for on-line operation. Much faster measurements are possible if accuracies of 2 to 5% are adequate.

Our method has the advantage of the flow system, that allows an easy and quick change of the sample to be examined with low residence time in high temperature zones that reduces decomposition and corrosion. It is possible to produce the phase separation at constant temperature and composition by both increasing and decreasing the pressure of the system. The problem of getting a representative sample is avoided and the method is faster than static vapor pressure measurements. When a solution of unknown vapor pressure is being studied, a quick preliminary run with decreasing pressure is recommended to roughly determine the two phase pressure.

This method is useful with a wide variety of fluid solutions. For example, we have used it successfully on other aqueous solutions of salts including KCl and CaCl$_2$, and also aqueous solutions of gases such as CO$_2$. Since the method and effects detected are basically mechanical and do not involve chemical reactions, the method is also applicable with any type fluid solutions having densities an viscosities in the range of utility of the specific densimeter used.

That which is claimed is:

1. A method of detecting the separation of a fluid into two or more phases comprising noting a decrease in the ratio of $(A - A°)/(\text{drive power})$ where A is the vibration amplitude and A° is an arbitrary constant of the tube containing the fluid vibrating under constant drive power.

* * * * *